(12) United States Patent
Lin et al.

(10) Patent No.: US 8,709,784 B2
(45) Date of Patent: Apr. 29, 2014

(54) **USE OF *LACTOBACILLUS* FOR LIVER PROTECTION**

(71) Applicant: China Medical University, Taichung (TW)

(72) Inventors: Wen-Hsin Lin, Nantou County (TW); Chi-Rei Wu, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 13/736,089

(22) Filed: Jan. 8, 2013

(65) Prior Publication Data

US 2014/0065114 A1    Mar. 6, 2014

(30) Foreign Application Priority Data

Aug. 29, 2012  (TW) .............................. 101131368 A

(51) Int. Cl.
*C12N 1/20*    (2006.01)

(52) U.S. Cl.
USPC ...................... 435/252.9; 424/93.45

(58) Field of Classification Search
USPC ...................... 435/252.9; 424/93.45
See application file for complete search history.

(56) References Cited

U.S. PATENT DOCUMENTS

| 3,953,609 | A | 4/1976 | Farr |
| 5,603,930 | A | 2/1997 | Brassart et al. |
| 6,491,956 | B2 | 12/2002 | Heo et al. |
| 7,507,572 | B2 | 3/2009 | Molin et al. |
| 2012/0020943 | A1 | 1/2012 | Lin |

*Primary Examiner* — Susan Hanley
*Assistant Examiner* — Nghi Nguyen
(74) *Attorney, Agent, or Firm* — CKC & Partners Co., Ltd.

(57) ABSTRACT

A method for liver protection of a mammal is provided and includes administering an effective amount of isolated *Lactobacillus plantarum* CMU995 thereto. Providing a new use of *Lactobacillus plantarum* CMU995, which is deposited at the Food Industry Research and Development Institute (FIRDI) in Taiwan under accession number BCRC 910472 and in the German Collection of Microorganisms and Cell Cultures (DSMZ) under accession number DSM 23780.

10 Claims, 11 Drawing Sheets

USE OF *LACTOBACILLUS* FOR LIVER PROTECTION

RELATED APPLICATIONS

The application claims priority to Taiwan Application Serial Number 101131368, filed Aug. 29, 2012, which is herein incorporated by reference.

BACKGROUND

1. Field of Invention

The present disclosure relates to a use of a *Lactobacillus*. More particularly, the present disclosure relates to a use of a *Lactobacillus plantarum*, strain CMU995, for liver protection.

2. Description of Related Art

*Lactobacillus* is one of the main bacteria existed in the intestinal tract of a human being or an animal. Because of the beneficial effects on the physiological activity of a human or an animal body, *Lactobacillus* is often added into various probiotic products. For example, *Lactobacillus* can inhibit the growth of enteric pathogens (such as *Salmonella* or *Escherichia*) or resist the invasion of the pathogens, for instance, preventing the invasion of *Salmonella typhimurium* to the gastrointestinal epithelial cells. There are many patents related to the applications of *Lactobacillus* for inhibiting the pathogens. For example, U.S. Pat. No. 5,603,930 discloses a *Lactobacillus johnsonii* that can inhibit enterotoxin and intestinal invasive pathogens; U.S. Pat. No. 3,953,609 discloses a *Lactobacillus lactis* that can inhibit the growth of *Escherichia* in the digestive system; and U.S. Pat. No. 6,491,956 discloses a *Lactobacillus acidophilus* that can prevent and treat gastritis, duodenal ulcer, and gastric ulcer caused by *Helicobacter pylori* infection.

Despite basic physiological/pharmacological activities, *Lactobacillus* must have two important characteristics to function effectively within the animal body. First, the *Lactobacillus* must have strong resistance to the gastric acid and choline secreted by the animal gastrointestinal tract to survive in the digestive system and reach to the intestinal tract to perform its function. Then, the *Lactobacillus* must be able to strongly adhere to the intestinal epithelial cells of an animal host to compete with other pathogens in the gastrointestinal tract and avoid being expelled by the pathogens, in addition, because the pathogens also adhere onto the intestinal epithelial cells and so infective to the host, the *Lactobacillus* would be able to effectively expel the pathogens to protect the gastrointestinal tract from being infected if the *Lactobacillus* has the even stronger adhesion ability to the intestinal epithelial cells.

The novel strain of *Lactobacillus plantarum*, which was first isolated by the inventors of the present invention, has been proven that, apart from the ability of inhibiting the pathogens, it has excellent adhesion ability to the cells of the gastrointestinal tract and the urinary tract through in vivo and in vitro experiments. Therefore, the *Lactobacillus plantarum* can effectively and durably protect the gastrointestinal tract and the urinary tract from pathogenic infections. It also been found that this strain can directly inhibit the growth of the pathogens to prevent and treat diseases caused by the pathogens.

SUMMARY

An aspect of the present disclosure is to provide a *Lactobacillus plantarum*, strain CMU995, namely *Lactobacillus plantarum* CMU995 in the followings, which is capable of preventing intestinal epithelial cell damages caused by intestinal endotoxin, thereby stabilizing the intestinal epithelial cells. In animal experiments, the *Lactobacillus plantarum* CMU995 is capable of inhibiting alcohol-induced endotoxin passing through intestines and then invading into blood. Therefore, the *Lactobacillus plantarum* CMU995 is able to inhibit alcohol or endotoxin-induced hepatitis or enteritis. It is worth to be mentioned that, results according to clinical experiments shows that the *Lactobacillus plantarum* CMU995 is also capable of decreasing levels of blood endotoxin and blood ammonia in patients with hepatocellular carcinoma or liver cirrhosis. Thus, the *Lactobacillus plantarum* CMU995 can be applied to treatments and/or preventions of diseases caused by alcohol and/or endotoxin.

According to one embodiment of the present disclosure, a method for liver protection of a mammal includes administering an effective amount of isolated *Lactobacillus plantarum* CMU995 to the mammal. The aforementioned *Lactobacillus plantarum* CMU995 is deposited at the Food Industry Research and Development Institute (FIRDI) in Taiwan under accession number BCRC 910472 and in the German Collection of Microorganisms and Cell Cultures (DSMZ) under accession number DSM 23780.

According to another embodiment of the present disclosure, a probiotic composition for liver protection comprises powdered *Lactobacillus plantarum* CMU995, in which the concentration of said powdered *Lactobacillus plantarum* CMU995 is $1 \times 10^5$ CFU/g to $1 \times 10^{12}$ CFU/g it is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
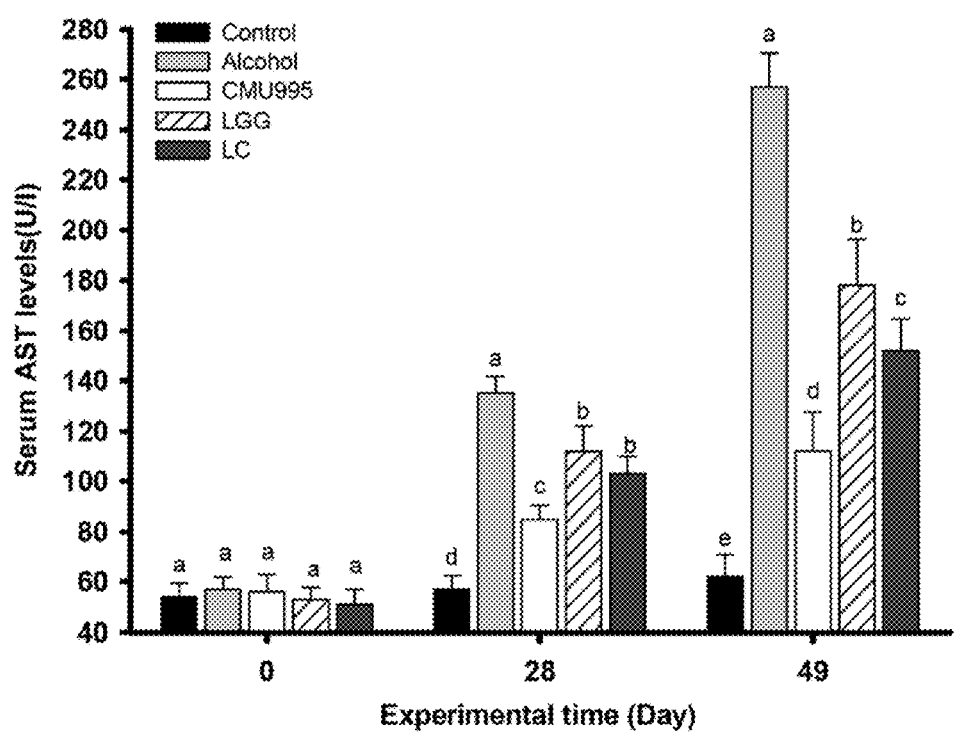
FIG. 1 is a bar chart illustrating different levels of AST (aspartate aminotransferase) in mice blood serum during an animal experiment according to example II of the present disclosure.

The present disclosure can be understood more clearly with the additional description which follows, which refers to non-limiting examples illustrating properties of a *Lactobacillus plantarum* strain, CMU995, named *Lactobacillus plantarum* CMU995 in the followings, in relation to liver and/or intestinal protection.

A novel use of the *Lactobacillus plantarum* CMU995 is provided for liver protection, in which said *Lactobacillus plantarum* CMU995 was screened out and elected earlier by the inventor of the present invention herein, and the *Lactobacillus plantarum* CMU995 was not readily available to the public at the time of invention. The *Lactobacillus plantarum* CMU995 is deposited at the Food Industry Research and Development Institute (FIRDI) in Taiwan, 331. Shih-Pin Road, Hsinchu, 300 Taiwan R.O.C., on Apr. 30, 2010, under accession number BCRC 910472, and in the German Collection of Microorganisms and Cell Cultures (DSMZ), Inhoffenstraβe 7B, 38124 Braunschweig, Germany, on Jul. 23, 2010, under accession number DSM 23780. DSMZ has been accepted for deposit under the Budapest Treaty on the International Recognition of Deposit of Microorganisms for the purpose of Patent Procedure. All restrictions on the availability to the public of the material so deposited will be irrevocably removed upon the granting of a patent.

Subsequent to deposit of strain DSM 23780, the taxonomic classification of *Lactobacillus plantarum* CMU995 is as follows;

| Taxonomy of *Lactobacillus plantarum* CMU995 DSM 23780 (Morphological and physiological characteristics) | |
|---|---|
| Characteristics of colony (2 days, MSR Agar) | Diameter of colony: 0.5~1 mm, white-gray, smooth |
| Cell form and length (MRS Bouillon) | Short rod-shaped |
| Adherent ability on the gastrointestinal epithelial cells | Strong |
| Lactic acid configuration | D |
| Growth at 15° C. | Positive |
| Growth at 45° C. | Positive |
| End Ph in MRS Bouillon | 3.5~4.2 |
| Gas formation out of glucose | Positive |
| Ammonia out of arginine | Negative |
| Diamino pimelic acid | Negative |

According to earlier results of regardless in vitro whether in vivo experiments, the aforementioned *Lactobacillus plantarum* CMU995 is capable of inhibiting pathogen activity. Additionally, the *Lactobacillus plantarum* CMU995 is also capable of adhering to intestinal as well as urethral epithelial cells with great adhesion efficiency, so that direct entries of pathogens into blood via intestine and urine can be prevented, thereby protecting intestine and urine.

Since alcohol commonly causes liver diseases, the *Lactobacillus plantarum* CMU995 is also able to prevent alcohol being intaken into blood and reduces blood alcohol, thereby protecting the liver. In addition, the *Lactobacillus plantarum* CMU995 can be incorporated into pharmaceutical compositions, food, or drinks. Furthermore, because that alcohol causes increments of intestinal pathogens and toxins, the *Lactobacillus plantarum* CMU995 may also inhibit the increments of intestinal pathogens and toxins as well, therefore further inhibiting toxins or pathogens to be uptaken by liver or other organs. In short, the *Lactobacillus plantarum* CMU995 can be widely used for toxin exclusion, removal, and liver protection.

The *Lactobacillus plantarum* CMU995 and a probiotic composition containing the *Lactobacillus plantarum* CMU995 is used for preventing hepatitis caused by alcohol and endotoxin, and reducing endotoxin-induced liver lesions and/or hepatocarcinogenesis. The probiotic composition can be supplied in a form of a pharmaceutical composition, a feed, a drink, a nutrient supplement, a diary, a food, or a healthy food. What is more, the aforementioned probiotic composition can be also provided in a form of a powder, a tablet, a granule, a suppository, a capsule, an ampoule, a liquid, or a spray. The probiotic composition containing the *Lactobacillus plantarum* CMU995 is capable of preventing or treating various diseases, and can be widely used to protect intestinal cells, reduce intestinal and blood toxin, and inhibit alcohol intake, thus protecting the liver.

EXAMPLES

The following examples are described for those skilled in the art to further understand the present disclosure and should not be limited to the present disclosure.

I. Adhesion Analysis (1) *Lactobacilli* Preparation

*Lactobacillus* strains used in this cell adhesion test includes *Lactobacillus plantarum* CMU995 of the present disclosure, *Lactobacillus rhamnosus* GG (LGG, ATCC 53103), *Lactobacillus plantarum* 299v, and *Lactobacillus casei* Shirota. Each of these strains were activated twice in MRS broth (DIFCO®) before transferring to 5 ml MRS broth for culturing. After culturing for 24 hours, 1 ml of each strain were centrifuged at 6,000 rpm for 10 minutes and then washed twice with phosphate buffer saline (PBS), pH 7.2. Then, concentrations of each cultured strain were adjusted to $10^9$ CFU (colony-forming unit)/ml in accordance with a value of $OD_{600}$ for further adhesion experiments.

(2) Cell Culture

Cell lines used herein are all kindly provided by the Bioresource Collection and Research Center, Taiwan, and include human colon adenocarcinoma (strain Caco-2 and HT-29), and gastric adenocarcinoma (strain AGS). The Caco-2 and HT-29 cells were cultured in DMEM cell culture medium with 10% fetal bovine serum, and the AGS cells were cultured in F-12 cell culture medium with 10% fetal bovine serum. These cells were all activated and stabilized before proceeding on further experiments.

(3) *Lactobacillus* Adhesion Analysis

The activated AGS, Caco-2, and HT-29 cells mentioned above were then seeded in a 96-well culture plate, respectively; each well of the 96-well culture plate containing 200 μl of corresponding culture media was seeded with about $10^4$ cells, and the culture media were being replaced with fresh media of the same composition every 24 hours. After culturing for 48 hours, 20 μl of each activated *Lactobacillus plantarum* CMU995, *Lactobacillus rhamnosus* GG (LGG, ATCC 53103), *Lactobacillus plantarum* 299v, and *Lactobacillus casei* Shirota were added to the cells respectively and incubated for 1 hour for adhesion, and then non-adhered *Lactobacilli* were discarded by washing with PBS three times. In each well, cells and the *Lactobacilli* adhered thereto were fixed with 10% formaldehyde for 30 minutes followed by wash with PBS three times. Subsequently, fixed *Lactobacilli* adhered cells were stained with crystal violet for 5 minutes followed by wash with 75% ethanol three times. Adhesion efficiencies were acquired by counting total amounts of adhered *Lactobacilli* onto 50 cells under randomized microscopic areas of a phase-contrast microscope; thereby an average amount of *Lactobacillus* adhering to each cell was calculated. The results are shown in Table 1.

TABLE 1

| strains | The amount of adhered *Lactobabilli* CFU/cell | | |
|---|---|---|---|
| | Caco-2 | HT-29 | AGS |
| *Lactobacillus plantarum* CMU995 | 53.6 ± 6.8 | 58.2 ± 10.5 | 51.7 ± 6.3 |
| LGG (ATCC 53103) | 7.5 ± 1.5 | 6.7 ± 2.9 | 4.4 ± 0.8 |
| *Lactobacillus casei* Shirota | 3.2 ± 3.4 | 5.5 ± 2.1 | 2.8 ± 3.0 |
| *Lactobacillus plantarum* 299v | 15.7 ± 3.5 | 16.5 ± 3.2 | 12.6 ± 2.4 |

As shown in Table 1, comparing to LGG (ATCC 53103), *Lactobacillus casei* Shirota, *Lactobacillus plantarum* 299v, obviously, the *Lactobacillus plantarum* CMU995 has significant adhesion ability to cell lines of whether strain Caco-2, HT-29, or AGS.

II. Animal Experiment (1) Animal Grouping 8-week old C57BL/6J mice were randomly divided into 5 groups with 8 mice in each group, and the initial weight of each mouse is 23±1 g. The 5 groups include:

Group A; Control group: The mice were freely fed with sterilized Lieber-DeCarli liquid diet without ethanol added, and were fed by 0.2 ml sterilized physiological saline solution every day.

Group B; Negative control group: The mice were freely fed with ethanol-containing sterilized Lieber-DeCarli liquid diet, and were fed by 0.2 ml sterilized physiological saline solution every day.

Group C; *Lactobacillus plantarum* CMU995 experimental group: The mice were freely fed with ethanol-containing sterilized Lieber-DeCarli liquid diet, and were fed by 0.2 ml of $2 \times 10^{10}$ CFU/ml *Lactobacillus plantarum* CMU995 every day.

Group D; *Lactobacillus rhamnosus* GG (LGG) experimental group: The mice were freely fed with ethanol-containing sterilized Lieber-DeCarli liquid diet, and were fed by 0.2 ml of $2 \times 10^{10}$ CFU/ml *Lactobacillus rhamnosus* GG every day.

Group E; *Lactobacillus casei* Shirota (LC) experimental group: The mice were freely fed with ethanol-containing sterilized Lieber-DeCarli liquid diet, and were fed by 0.2 ml of $2 \times 10^{10}$ CFU/ml *Lactobacillus casei* Shirota every day.

(2) *Lactobacilli* Preparation

Each *Lactobacillus casei* Shirota, *Lactobacillus plantarum* 299v, *Lactobacillus rhamnosus* GG, and *Lactobacillus plantarum* CMU995 were lyophilized into powder with a concentration of $1 \times 10^{11}$ CFU/g, and were all stored in 4° C. These lyophilized *Lactobacillus* powder were freshly prepared before feeding experimental mice daily by re-suspending and dissolving them in sterilized physiological saline solution to a final concentration of $2 \times 10^{10}$ CFU/ml.

(3) *Lactobacilli* Feeding and Hepatitis Induction

At the beginning of this experiment, mice of each group were freely fed with Lieber-DeCarli liquid diet for a week. Subsequently, mice of each group were started to be fed with 0.2 ml of different experimental samples daily; mice of group A and group B were fed with physiological saline solution daily, and mice of group C, group D, and group E were fed with different freshly prepared probiotic solutions daily, that is, the *Lactobacillus plantarum* CMU995, the *Lactobacillus rhamnosus* GG, and the *Lactobacillus casei* Shirota, respectively. Hepatitis induction was started at day 3, and mice of group B, group C, group D, and group E were started to be fed with ethanol-containing Lieber-DeCarli liquid diet. The concentration of ethanol of such an ethanol-containing Lieber-DeCarli liquid diet ranges from 1.25% to 5%; the concentration increases 1.25% every two days till the highest concentration (5%). These mice received the highest ethanol concentration (5%) for a total of six weeks, and the total duration of the hepatitis induction is seven weeks.

(4) Animal Sacrifice and Sample Preparation

The day of the mice started to be fed with ethanol-containing Lieber-DeCarli liquid diet is defined as day 0, and the mice were sacrificed after seven weeks (49 days). Appropriate amounts of blood samples of the mice were collected at day 0 and day 28 via facial vein in mice, and the mice were fasted one day before the day of sacrifice. The mice were sacrificed by cervical dislocation, and whole blood samples were collected. Liver samples and large intestine samples of the mice were collected, frozen, and stored at −80° C.

(5) Blood, Liver, and Intestinal Samples Analysis

Appropriate amounts of frozen liver and intestinal samples were respectively placed on a mortar and grinded with liquid nitrogen, and then these samples were collected and mixed with appropriate amounts of HEPES buffer for further analytical experiments. The blood samples were centrifuged at low speed thereby isolating the blood serum for further analytical experiments. Analysis of blood samples including aspartate aminotranferase (AST), alanine aminotransferase (ALT), trglyceride (TG), cholesterol, endotoxin, and cytokine TNF-α, were analyzed by using an automated hematology analyzer (Cobas Mira Plus analyzer, Roche, USA) and/or enzyme-linked immunosorbent assay (ELISA).

(6) Statistical Analysis

Statistical analyses of the experimental results were performed using Statistical Analysis System, V. 8.02 for Windows, 2001, with analysis of variance (ANOVA) test. A significant threshold of $P<0.05$ was employed for the ANOVA analyses. The diagrams and figures performing the experimental results were performed using SigmaPlot 10.0.

Animal Experiment Results

Figure 2:
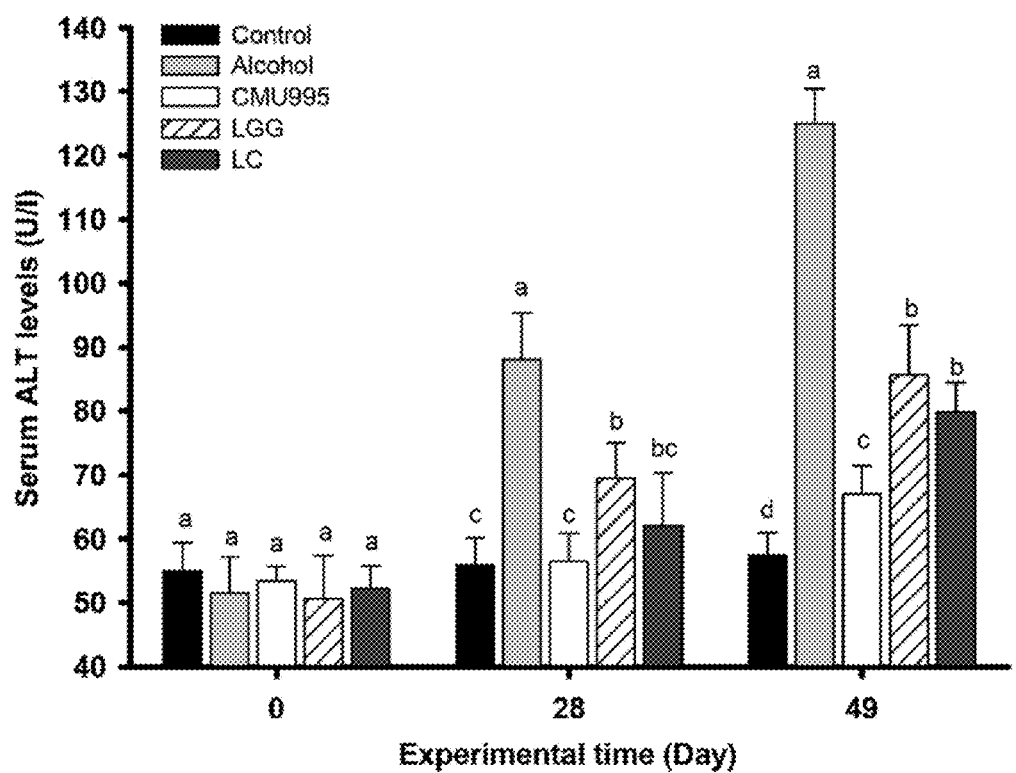
FIG. 2 is a bar chart illustrating different levels of ALT (alanine aminotransferase) in mice blood serum during an animal experiment according to example II of the present disclosure.

FIG. 1 and FIG. 2 are bar charts showing different levels of aspartate aminotransferase (AST) and alanine aminotransferase (ALT) in blood serum, respectively, of mice of group A to group E according to the animal experiment of the present disclosure. Levels of AST and ALT of the hepatitis-induced and *Lactobacillus plantarum* CMU995 fed mice (Group C) were significantly lower than those of the group B, group D, and group E, which were also hepatitis induced. Therefore, the *Lactobacillus plantarum* CMU995 is capable of reducing the AST and ALT level in hepatitis-induced mice blood serum, so that it is capable of avoiding alcohol-caused liver damages, thereby protecting the liver.

Figure 3:
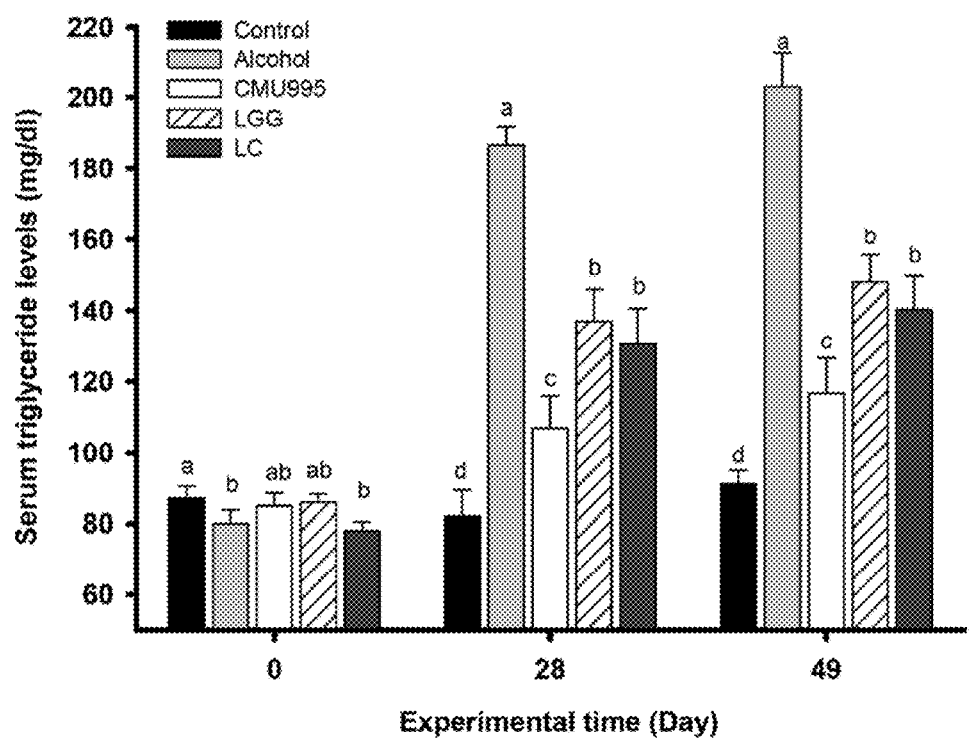
FIG. 3 is a bar chart illustrating different levels of triglyceride in mice blood serum during an animal experiment according to example II of the present disclosure.
Figure 4:
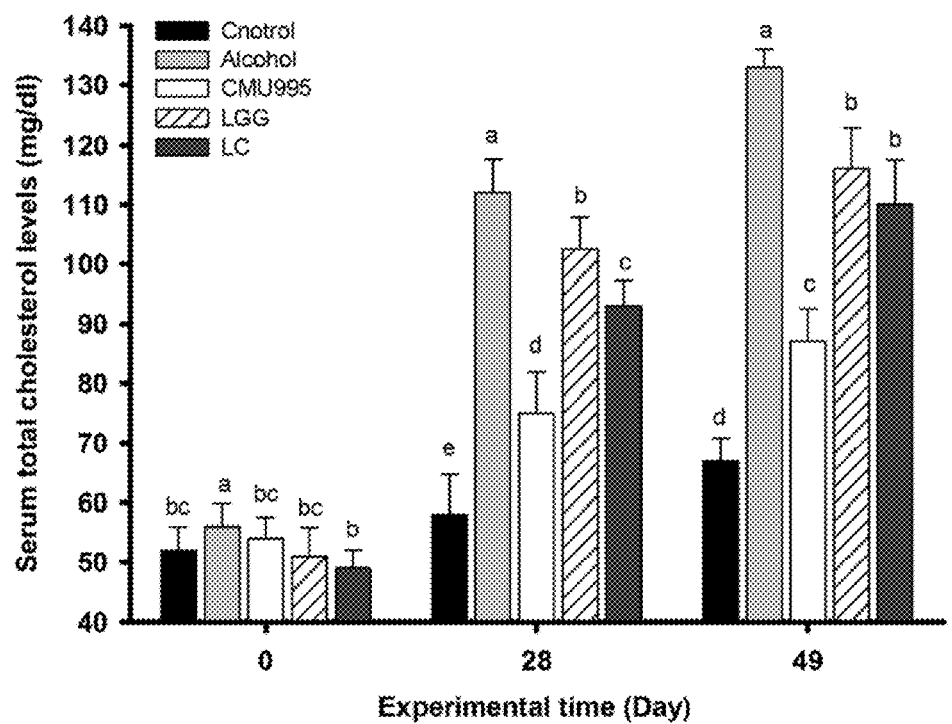
FIG. 4 is a bar chart illustrating different levels of cholesterol in mice blood serum during an animal experiment according to example II of the present disclosure.

FIG. 3 and FIG. 4 are bar charts showing different levels of triglyceride and cholesterol in blood serum, respectively, of mice of group A to group E according to the animal experiment of the present disclosure. Levels of triglyceride and cholesterol of the hepatitis-induced and *Lactobacillus plantarum* CMU995 fed mice (Group C) were significantly lower than those of the group B, group D, and group E, which were also hepatitis induced. Therefore, the *Lactobacillus plantarum* CMU995 is capable of reducing the triglyceride and cholesterol level in hepatitis-induced mice blood serum, so that it is capable of avoiding alcohol-caused hyperlipidemia, thereby protecting the liver.

Figure 5:
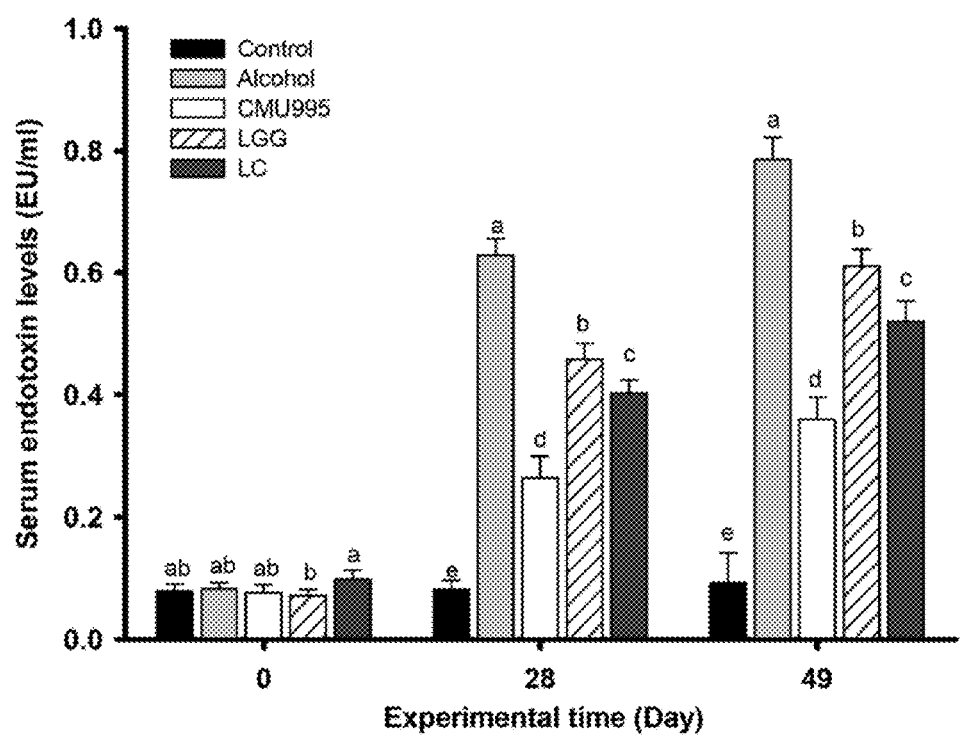
FIG. 5 is a bar chart illustrating different levels of endotoxin in mice blood serum during an animal experiment according to example II of the present disclosure.
Figure 6:
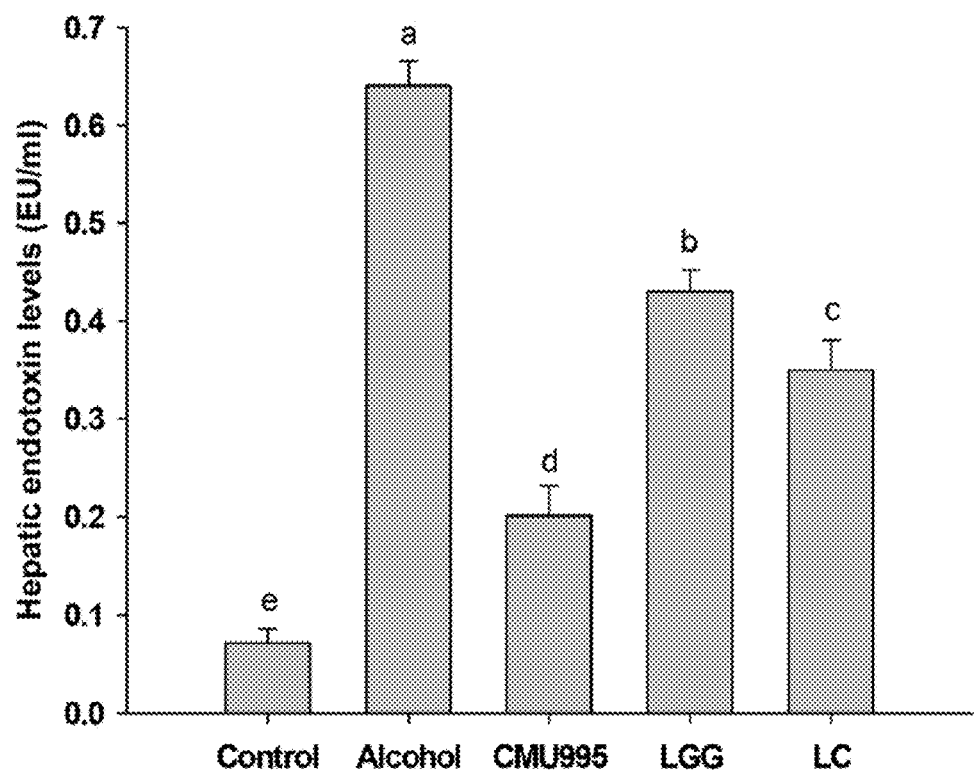
FIG. 6 is a bar chart illustrating different levels of endotoxin in mice liver during an animal experiment according to example II of the present disclosure.

FIG. 5 and FIG. 6 are bar charts showing different levels of endotoxin in blood serum and liver, respectively, of mice of group A to group E according to the animal experiment of the present disclosure. Levels of blood serum endotoxin and liver endotoxin of the hepatitis-induced and *Lactobacillus plantarum* CMU995 fed mice (Group C) were significantly lower than those of the group B, group D, and group E, which were also hepatitis induced. Therefore, the *Lactobacillus plantarum* CMU995 is capable of reducing the blood serum endotoxin and liver endotoxin level in hepatitis-induced mice, so that it is capable of avoiding entries of alcohol-induced endotoxin into blood, thereby protecting the liver.

Figure 7:
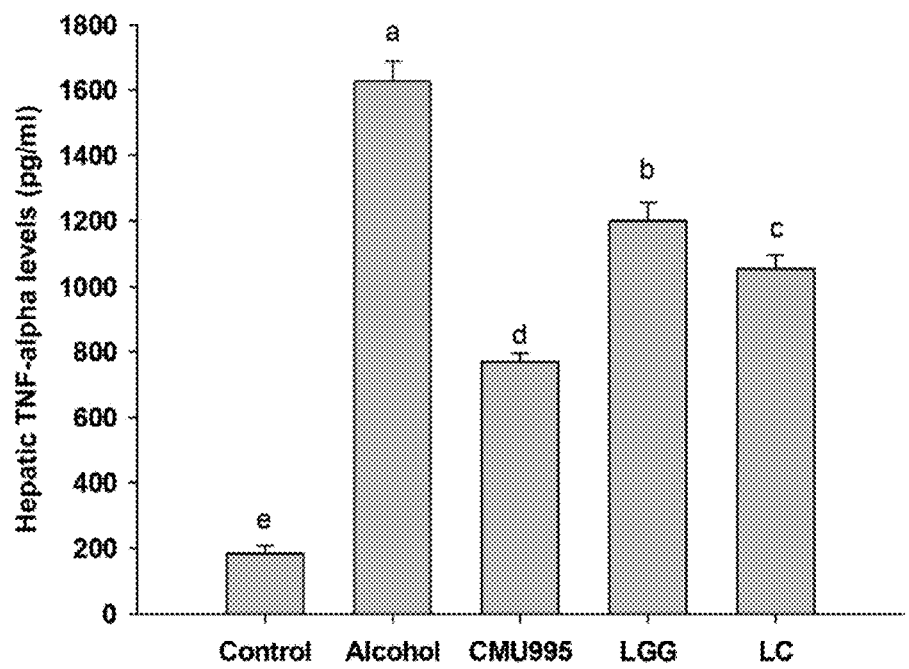
FIG. 7 is a bar chart illustrating different levels of cytokine TNF-α in mice liver during an animal experiment according to example II of the present disclosure.
Figure 8:
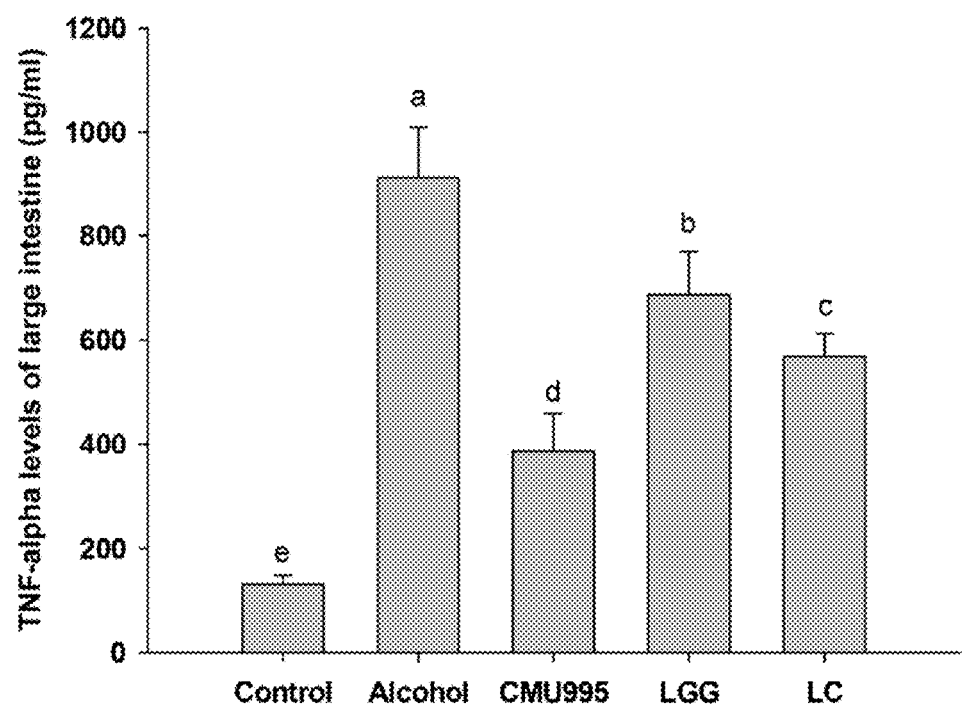
FIG. 8 is a bar chart illustrating different levels of cytokine TNF-α in mice large intestine during an animal experiment according to example II of the present disclosure.

FIG. 7 and FIG. 8 are bar charts showing different levels of liver and large intestinal cytokine TNF-α, respectively, of mice of group A to group E according to the animal experiment of the present disclosure. Levels of liver and intestinal cytokine TNF-α of the hepatitis-induced and *Lactobacillus plantarum* CMU995 fed mice (Group C) were significantly lower than those of the group B, group D, and group E, which were also hepatitis induced. Therefore, the *Lactobacillus plantarum* CMU995 is capable of reducing the liver and intestinal cytokine TNF-α level in hepatitis-induced mice, so that it is capable of reducing inflammation of liver and intestine.

III. Clinical Trial

In this clinical trial, 26 patients were included. Blood samples from each patient were collected before and after 4-week oral administration of a probiotic composition containing the *Lactobacillus plantarum* CMU995 for further analysis.

(1) Exclusion and Inclusion Conditions of Patients

Patients in this clinical trial should have met all the following criteria for inclusion; with confirmed cirrhosis, age between 30-70 years old.

Patients were excluded from this trial if they met any one of the following conditions:

1. Those with underling portal hypertension, such as hepatorenal syndrome, or bacterial peritonitis.
2. Those with neurological disease and acute metabolic disease, such as stroke, cardiac failure, respiratory failure, acute renal failure, or ichorrhemia.
3. Those with stage 3 to stage 4 severe hepatic coma.
4. Those with systemic disorders such as cancers, cardiopulmonary dysfunction, renal insufficiency.
5. Those who had been treated with probiotics-related compositions or products.
6. Women who are pregnant or may possibly become pregnant or are lactating under a positive urine pregnant test.

(2) Probiotic Composition

The probiotic composition used in this clinical trial contains the *Lactobacillus plantarum* CMU995 and other excipients. Each unit of the aforementioned probiotic composition contains 3 g powder including $3\times10^{10}$ CFU *Lactobacillus plantarum* CMU995, so that the concentration of *Lactobacillus plantarum* CMU995 of each unit of the probiotic composition is $1\times10^{10}$ CFU/g.

(3) Sample Analysis 26 patients were participated in the clinical trial and had signed a consent form. An amount of the probiotic composition for the 4-week clinical trial was provided for the patients, and each of the patients was treated with one unit of the probiotic composition after each meal. Blood samples of the patients were collected after 4 weeks for analysis including levels of cytokine TNF-α, endotoxin, and blood ammonia, in order to evaluate the effects caused by probiotic composition. The statistical analyses of the results were performed by using SigmaPlot 10.0.

Results

Figure 9A:
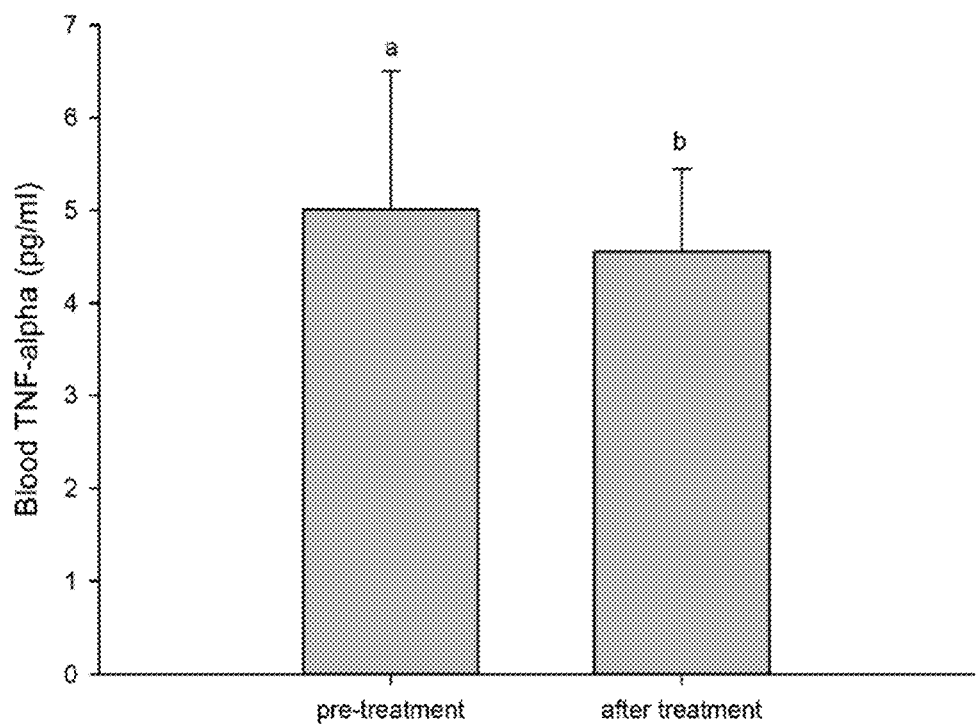
FIG. 9a is a bar chart illustrating different levels of cytokine TNF-α of the blood samples from cirrhosis patients being treated with the probiotic composition according to a clinical trial of example II of the present disclosure.
Figure 9B:
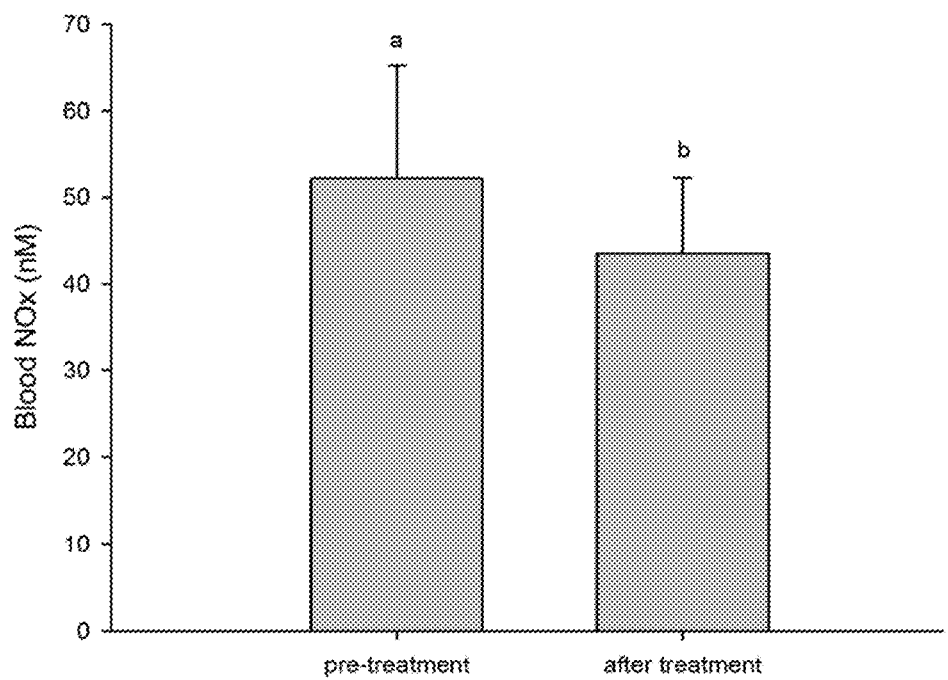
FIG. 9b is a bar chart illustrating different levels of blood ammonia of the blood samples from cirrhosis patients being treated with the probiotic composition according to a clinical trial of example II of the present disclosure.
Figure 9C:
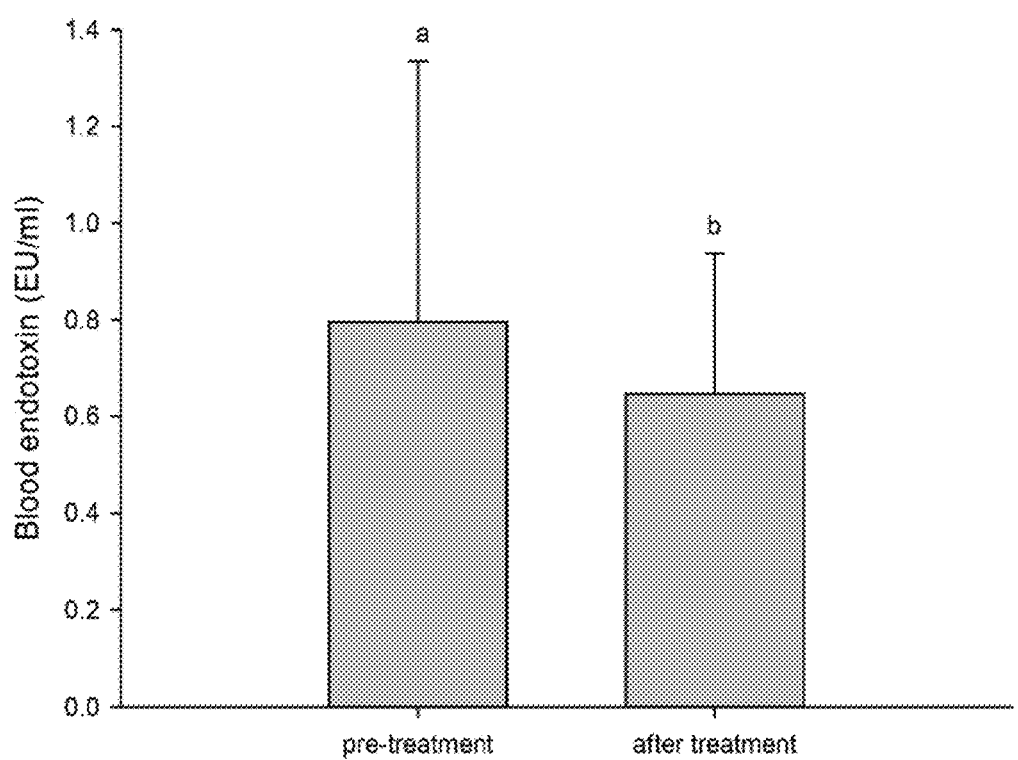
FIG. 9c is a bar chart illustrating different levels of endotoxin, of the blood samples from cirrhosis patients being treated with the probiotic composition according to a clinical trial of example II of the present disclosure.

FIG. 9a to FIG. 9c are bar charts showing different levels of cytokine TNF-α, blood ammonia, and endotoxin, respectively, of the blood samples from the cirrhosis patients who had been treated with the probiotic composition. After treating the patients with the probiotic composition for 4 weeks, the levels of cytokine TNF-α, blood ammonia, and endotoxin significantly decreased (letter "a" differs from letter "b" means that the results before and after probiotic composition treatments are statistically significant, that is, $p<0.05$). Therefore, it had been proven that, by treating cirrhosis patients with the probiotic composition containing the *Lactobacillus plantarum* CMU995 of the present disclosure, blood quality of the cirrhosis patients have been significantly improved.

Advantages of the *Lactobacillus plantarum* CMU995 of the present disclosure are described as follows:

1. The *Lactobacillus plantarum* CMU995 of the present disclosure is salt and acid tolerant, and can be well-adhered to intestinal epithelial cells of an animal host, so that the *Lactobacillus plantarum* CMU995 can survive in gastrointestinal system permanently. Therefore, the *Lactobacillus plantarum* CMU995 may competitively inhibit pathogens adhere to the intestinal epithelial cells. Furthermore, referring to the aforementioned results of the adhesion analysis, the clinical trial, and the animal experiment, the *Lactobacillus plantarum* CMU995 is capable of preventing damages of cells caused by exotoxins or endotoxins, thereby stabilizing the intestinal epithelial cells. The *Lactobacillus plantarum* CMU995 is also capable of blocking alcohol (ethanol) and/or toxins passing through intestines and then invading into blood.

2. For preventive use, the *Lactobacillus plantarum* CMU995 can be supplied in a form of a pharmaceutical composition, a feed, a drink, a nutrient supplement, a diary, a food, or a healthy food, so that the *Lactobacillus plantarum* CMU995 can be adhered to intestinal epithelial cells thereby blocking endotoxins, alcohol, or pathogens invading into blood, and thus providing effects of protecting the liver, reducing blood endotoxin, blood alcohol, and so on.

3. For therapeutic use, *Lactobacillus plantarum* CMU995-containing drugs or foods can be administered to those who had been invaded by pathogens, alcohol, or other toxins which cause diseases, so that pathogens, alcohol, or other toxins can be effectively reduced, or even removed. For example, liver cancer or hepatitis patients can be treated with the *Lactobacillus plantarum* CMU995 for reducing phenomena of hyperammonemia, liver inflammation, or intestinal inflammation. In short, the *Lactobacillus plantarum* CMU995 is capable of preventing or curing gastrointestinal diseases caused by toxins or alcohol.

4. The *Lactobacillus plantarum* CMU995 not only can inhibit intestinal toxins invading into blood by stabilizing the intestinal epithelial cells, it may also reduce bacterial or toxin accumulation in intestines, and thus one who had intaken the *Lactobacillus plantarum* CMU995 can be protected by a synergetic effect of these aforementioned detox mechanisms. The word "detox" means that to expel various toxins, and these toxins are harmful substances, mycotoxins, and carcinogens, etc, such as intestinal endotoxins, hemotoxins, intestinal pathogens, alcohol, hazardous medicines, chemical hazardous substances, DEHP, etc. These toxins may invade into blood and transfer to other organs in an animal or a human body, and thus damages of organs such as liver will be caused. The *Lactobacillus plantarum* CMU995 and compositions containing the *Lactobacillus plantarum* CMU995 are also capable of accelerating the removal of intestinal or blood harmful substances, pathogens, or alcohol from body.

5. Because that the *Lactobacillus plantarum* CMU995 is able to inhibit toxins invade into blood, and to accelerate the removal of toxins, it is able to be widely applied to various medical and health related products. Therefore, a probiotic composition which contains the *Lactobacillus plantarum* CMU995 is also provided in the present disclosure. This probiotic composition can be used to inhibit absorption of various types of toxins, alcohol, and can also be used to inhibit pathogens by competitive inhibition.

6. The *Lactobacillus plantarum* CMU995 can be used to inhibit various gastrointestinal harmful substances such as toxins released from bacteria, toxins released from fungi, toxins released from viruses, toxins released from foods, alcohol, pesticides, drugs, food additives, chemical hazardous substances, and DEHP, especially alcohol and microorganisms released toxins.

7. The probiotic composition which contains the *Lactobacillus plantarum* CMU995 of the present disclosure can be in the form of a pharmaceutical composition, a feed, a drink, a nutrient supplement, a diary, a food, or a healthy food. Besides, the *Lactobacillus plantarum* CMU995 can be also added to various kinds of food, such as dairy products, etc.

8. Further, addictives can also be added to the probiotic composition of the present disclosure for enhancing the adherent efficiency of the *Lactobacillus plantarum* CMU995, thereby enhancing prevention of toxins invading into blood, and accelerating removal of toxins. Nutrient supplements and/or pharmaceutical supplements may also be added to this probiotic composition to increase the range of its use. For example, kinds of vitamins, Chinese herbal medicines, or other probiotics, etc, can be added to this probiotic composition, to enhance the removal of toxins or liver metabolism. Any addictives without negative effects can be added and mixed with the probiotic composition to perform synergetic effects of those.

9. The *Lactobacillus plantarum* CMU995 and the probiotic composition containing the *Lactobacillus plantarum* CMU995 can be administered to an animal or a human body in the form of a pharmaceutical composition, a feed, a drink, a nutrient supplement, a diary, a food, or a healthy food, in order to protect intestinal epithelial cells, reduce intestinal toxins, reduce blood toxins, reduce alcohol absorption, protect the liver and other organs in an animal or a human body, thereby preventing or curing diseases.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the invention. In view of the foregoing, it is intended that the present disclosure cover modifications and variations of this invention provided they fall within the scope of the following claims.

What is claimed is:

1. A method for treating a liver of a mammal affected by hepatitis, alcohol, or an endotoxin comprising administering an effective amount of isolated *Lactobacillus plantarum* CMU995 thereto, wherein the *Lactobacillus plantarum* CMU995 is deposited at the Food Industry Research and Development Institute (FIRDI) in Taiwan under accession number BCRC 910472 and in the German Collection of Microorganisms and Cell Cultures (DSMZ) under accession number DSM 23780.

2. The method according to claim 1, wherein the *Lactobacillus plantarum* CMU995 decreases levels of aspartate aminotransferase (AST) and/or alanine aminotransferase (ALT) in blood thereby treating the liver.

3. The method according to claim 1, wherein the *Lactobacillus plantarum* CMU995 decreases levels of cholesterol in blood and/or liver thereby treating the liver.

4. The method according to claim 1, wherein the *Lactobacillus plantarum* CMU995 decreases a level of blood triglyceride thereby treating the liver.

5. The method according to claim 1, wherein the *Lactobacillus plantarum* CMU995 decreases a level of blood alcohol thereby treating the liver.

6. The method according to claim 1, wherein the *Lactobacillus plantarum* CMU 995 decreases a level of endotoxin in blood thereby treating the liver.

7. The method according to claim 1, wherein the *Lactobacillus plantarum* CMU995 decreases a level of endotoxin in liver thereby treating the liver.

8. The method according to claim 1, wherein the *Lactobacillus plantarum* CMU995 decreases a level of cytokine TNF-α in blood thereby treating the liver.

9. The method according to claim 1, wherein the hepatitis is caused by alcohol, cytokine TNF-α, or endotoxin, thereby treating the liver.

10. The method according to claim 1, wherein the mammal is a human.

* * * * *